(12) United States Patent
Gaddam et al.

(10) Patent No.: US 10,119,986 B2
(45) Date of Patent: Nov. 6, 2018

(54) TIME AND FREQUENCY DOMAIN BASED STEP COUNTER

(71) Applicant: NXP B.V., Eindhoven (NL)

(72) Inventors: Vasanth Gaddam, Fremont, CA (US); Yifeng Zhang, San Jose, CA (US); Jie Zhang, Beijing (CN); Yuanwei Wu, Beijing (CN); Guanqing Wang, Beijing (CN)

(73) Assignee: NXP B.V., Eindhoven (NL)

( * ) Notice: Subject to any disclaimer, the term of this patent is extended or adjusted under 35 U.S.C. 154(b) by 255 days.

(21) Appl. No.: 14/722,319

(22) Filed: May 27, 2015

(65) Prior Publication Data

US 2018/0203032 A1 Jul. 19, 2018

Related U.S. Application Data

(63) Continuation of application No. 14/681,438, filed on Apr. 8, 2015.

(60) Provisional application No. 61/985,469, filed on Apr. 29, 2014, provisional application No. 61/985,470, filed on Apr. 29, 2014, provisional application No. 61/985,471, filed on Apr. 29, 2014.

(51) Int. Cl.
| | |
|---|---|
| *G01P 15/00* | (2006.01) |
| *G01C 22/00* | (2006.01) |
| *H01L 29/66* | (2006.01) |
| *H01L 21/3213* | (2006.01) |
| *H01L 29/78* | (2006.01) |

(52) U.S. Cl.
CPC ............ *G01P 15/00* (2013.01); *G01C 22/006* (2013.01); *H01L 21/32139* (2013.01); *H01L 29/6653* (2013.01); *H01L 29/6656* (2013.01); *H01L 29/66545* (2013.01); *H01L 29/66795* (2013.01); *H01L 29/7851* (2013.01)

(58) Field of Classification Search
CPC ... G01P 15/00; G01C 22/006; H01L 29/6656; H01L 29/66545; H01L 29/66795; H01L 29/7851; H01L 29/665; H01L 21/32139
USPC ........................................................ 702/141
See application file for complete search history.

(56) References Cited

U.S. PATENT DOCUMENTS

| | | | | |
|---|---|---|---|---|
| 5,583,776 A | * | 12/1996 | Levi ..................... | A43B 3/0005 701/300 |
| 7,981,058 B2 | * | 7/2011 | Akay ................... | A61B 5/0002 600/595 |
| 2003/0161443 A1 | | 8/2003 | Xiao et al. | |

(Continued)

OTHER PUBLICATIONS

Non Final Office Action dated Jun. 26, 2017 for U.S. Appl. No. 14/722,319 18 pages.

(Continued)

*Primary Examiner* — Nikolay Yushin

(57) ABSTRACT

A system for counting steps comprising a 3-D accelerometer is disclosed. The system also includes a pre-processor module coupled to the 3-D accelerometer and a dominant component computation unit coupled to the pre-processor module. The dominant component computation unit is configured to identify a dominant component in an output of the 3-D accelerometer. The system further includes a step counter for counting a number of steps using the output of the dominant component computation unit. The step counter includes a Fast Fourier Transform (FFT) module and a direct current (DC) remover module to remove a static component from the output of the FFT module. The step counter also includes a derivative filter and a zero crossing detector.

20 Claims, 14 Drawing Sheets

(56) References Cited

U.S. PATENT DOCUMENTS

| | | | |
|---|---|---|---|
| 2004/0203472 A1 | 10/2004 | Chien | |
| 2008/0288200 A1* | 11/2008 | Noble | A61B 5/1116 |
| | | | 702/96 |
| 2009/0265297 A1* | 10/2009 | Misra | G06N 99/005 |
| | | | 706/52 |
| 2010/0082288 A1* | 4/2010 | Cattin | A43B 3/0005 |
| | | | 702/150 |
| 2011/0077017 A1* | 3/2011 | Yu | H04L 5/0007 |
| | | | 455/452.1 |
| 2013/0013249 A1* | 1/2013 | Hagiwara | G01P 13/00 |
| | | | 702/141 |
| 2013/0103641 A1 | 4/2013 | Rehman | |
| 2013/0158686 A1* | 6/2013 | Zhang | G01C 22/006 |
| | | | 700/91 |
| 2013/0190903 A1* | 7/2013 | Balakrishnan | A61B 5/7246 |
| | | | 700/91 |
| 2013/0217979 A1* | 8/2013 | Blackadar | A61B 5/0024 |
| | | | 600/301 |
| 2014/0100465 A1 | 4/2014 | Kim et al. | |

OTHER PUBLICATIONS

Final Office Action dated Dec. 18, 2017 for U.S. Appl. No. 14/722,319 12 pages.
Advisory Action dated Mar. 8, 2018 for U.S. Appl. No. 14/868,252, 4 pages.

\* cited by examiner

TIME AND FREQUENCY DOMAIN BASED STEP COUNTER

CROSS-REFERENCE TO RELATED APPLICATION

This application is a continuation of application Ser. No. 14/681,438 filed on Apr. 8, 2015 which claims the benefit of U.S. Provisional Application No. 61/985,469, filed Apr. 29, 2014, U.S. Provisional Application No. 61/985,470, filed Apr. 29, 2014 and U.S. Provisional Application No. 61/985,471, filed Apr. 29, 2014, all of them are being incorporated herein by reference

BACKGROUND

In recent years, there has been an increasing need to use technologies to monitor health and fitness. Providing users with real-time and accurate information about their daily activities in a non-intrusive manner has become a promising approach. Using these technologies for tracking activities, users can adjust their daily activities, to meet their personal fitness goals, for example. Also, in casual and competitive sports, users want to see their performance (e.g., running speed, jump height, stride length, etc.) in real-time and make adjustments in their training routine to meet the performance goals. The implementation of activity tracking relies on the use of sensors. The sensors may include accelerometers, gyroscopes, magnetometers, barometers, temperature sensor, etc. To allow continuous tracking of user activities, the sensors are normally worn on the user's body. These sensors can be placed on one or multiple locations on the user's body depending on the application. To be more useful, the activities are tracked continuously for a prolonged period of time.

BRIEF SUMMARY

A method and apparatus for step counting based on time domain and frequency domain processing are disclosed. Embodiments according to the present invention can be used to improve information accuracy for the activity tracking.

In one embodiment, a system for counting steps comprising a 3-D accelerometer is disclosed. The system also includes a pre-processor module coupled to the 3-D accelerometer and a dominant component computation unit coupled to the pre-processor module. The dominant component computation unit is configured to identify a dominant component in an output of the 3-D accelerometer. The system further includes a step counter for counting a number of steps using the output of the dominant component computation unit. The step counter includes a Fast Fourier Transform (FFT) module and a direct current (DC) remover module to remove a static component from the output of the FFT module. The step counter also includes a derivative filter and a zero crossing detector.

In some embodiments, the system may also include a statistics generator module coupled to the dominant component computation unit and the pre-processor module. A classifier is included for determining an activity based on outputs of the dominant component computation unit and the statistics generator module. The step counter is configured to refine an output of the step counter based on an output of the classifier. A post-processor is also included to further refine an output of the step counter.

The statistics generator includes a first statistics module and a second statistics module, wherein the first statistics module is configured to generate statistics and frequency domain transformation based on an output of the dominant component computation unit and the second statistics module is configured to generate statistics and frequency domain transformation based on an output of the pre-processor module.

The pre-processor is configured to remove at least one of a direct current (DC) component in a vector sample received from the 3-D accelerometer and a high frequency component from the vector sample. The dominant component computation unit is configured to determine a dominant component in the vector sample. The vector sample includes a horizontal component and a vertical component. The vertical component is proportional to a vector inner product between a mean vector of a plurality of vector samples along three axes and each dynamic vector corresponding to a first difference between each of the plurality of vector samples and the mean vector. The horizontal component is related to a norm of a second difference between the first difference and the mean vector scaled by the vertical component.

In another embodiment, a non-transitory computer readable media including programming instruction which when executed by a processor performs an operation of counting steps is disclosed. The operation includes receiving an output from a 3-D accelerometer and pre-processing the received output of the 3-D accelerometer. The pre-processing includes removing a direct current (DC) component from the output of the 3-D accelerometer. The operation further includes determining a dominant component in the output of the 3-D accelerometer after the pre-processing. The output of the 3-D accelerometer is used to derive a vertical component and a horizontal component, the vertical component is proportional to a vector inner product between a mean vector of a plurality of vector samples along three axes and each dynamic vector corresponding to a first difference between each of the plurality of vector samples and the mean vector. The horizontal component is related to a norm of a second difference between the first difference and the mean vector scaled by the vertical component. The operation further includes counting steps using the dominant component, wherein the counting includes performing a Fast Fourier Transform (FFT) and zero crossing detection.

The pre-processor module may include a level normalization module, a DC notch filter and a low pass filter. The normalization module is configured to remove a gravity component from the output of the 3-D accelerometer.

According to some embodiments, the method for activity detection or activity tracking is based on statistical features extracted from vector samples of a subject, a dominant component of the vector samples, or both the vector samples and the dominant component. The method comprises collecting the vector samples from a 3-D (3-dimension) accelerometer attached to a subject; computing a dominant component; calculating the statistical features; and identifying an activity class based on the statistical features. The dominant component corresponds to a vertical component or a horizontal component. The vertical component is proportional to a vector inner product between a mean vector of the vector samples along three axes and each dynamic vector corresponding to a first difference between each vector sample and the mean vector. The horizontal component is related to a norm of a second difference between the first difference and the mean vector scaled by the vertical component. The vector sample collection may be performed at a pre-defined sample rate or a dynamic rate adjusted according to a detected or predicted activity of the subject. The identifying may comprise a first and a last stage to determine the activity class. The activity class is identified in the last stage associated with a classification result of the first stage.

The method may further comprise pre-processing the vector samples before the vector samples are used for said computing the dominant component. The pre-processing may normalize the vector samples to gravity and filtering the samples. The filtering operation may remove DC (direct current) components present in the vector samples, high frequency noise or low frequency noise of the vector samples. The method may also comprise a post-processing process performed after identifying the activity class.

Each statistical feature may be selected associated with a minimum overlap on value ranges among all activities. The activity class is identified associated with a classifier. The classifier may use training data to generate a cumulative distribution plot for each statistical feature. The cumulative distribution plot may be divided into multiple sections associated with first values of each statistical features and second values of all the statistical features related to one particular activity. Each section corresponds to a ratio range of the first values to the second values. The multiple sections may correspond to five sections. The five sections may correspond to (0-5%], (5%-10%], (10%-90%], (90%-95%] and (95-99%].

Each of the statistical features may be calculated based on individual axis accelerometer data of the vector samples, combined accelerometer data of the vector samples, the vertical component or the horizontal component. The statistical features may comprise a time domain mean value of the vector samples, a variance of the dominant component and time domain energy of vector samples without the DC components.

The activity class may be identified associated with a highest value among multiple metrics of all activities. Each metric is determined by combining values of each statistical feature with corresponding section dependent weights. The section dependent weights are pre-determined or dynamically adjusted.

According to another embodiment, the method for activity detection or activity tracking is based on statistical features extracted from frequency-domain data of vector samples only. The statistical features may also be extracted from frequency-domain data together with time-domain data of the vector samples, a dominant component of the vector samples, or both. The method comprises collecting vector samples from a 3-D (3-dimension) accelerometer attached to a subject; transforming the vector samples to frequency-domain samples; calculating the statistical features associated with the frequency-domain samples; identifying an activity class based on the statistical features.

The method may also comprise pre-processing the vector samples, computing a dominant component before the transformation; and a post-processing process after said identifying the activity class.

The frequency-domain samples may be calculated based on combined accelerometer data of the vector samples, the vertical component or the horizontal component. At least one of the statistical features may be selected from a peak, a location of the peak and sub-band frequency domain energy of the frequency domain samples. An example statistical feature set may comprise a time domain mean value, a variance of the dominant component, time domain energy of the vector samples without the DC components, and sub-band frequency-domain energy of the frequency-domain samples.

The dominant component is computed based on the vector samples. The dominant component corresponds to a vertical component or a horizontal component based on the sensor location on the body (e.g., foot, wrist, waist). The vertical component is proportional to a vector inner product between a mean vector of the vector samples along three axes and each dynamic vector corresponding to a first difference between each vector sample and the mean vector. The horizontal component is related to a norm of a second difference between the first difference and the mean vector scaled by the vertical component.

DETAILED DESCRIPTION OF THE INVENTION

Figure 1:
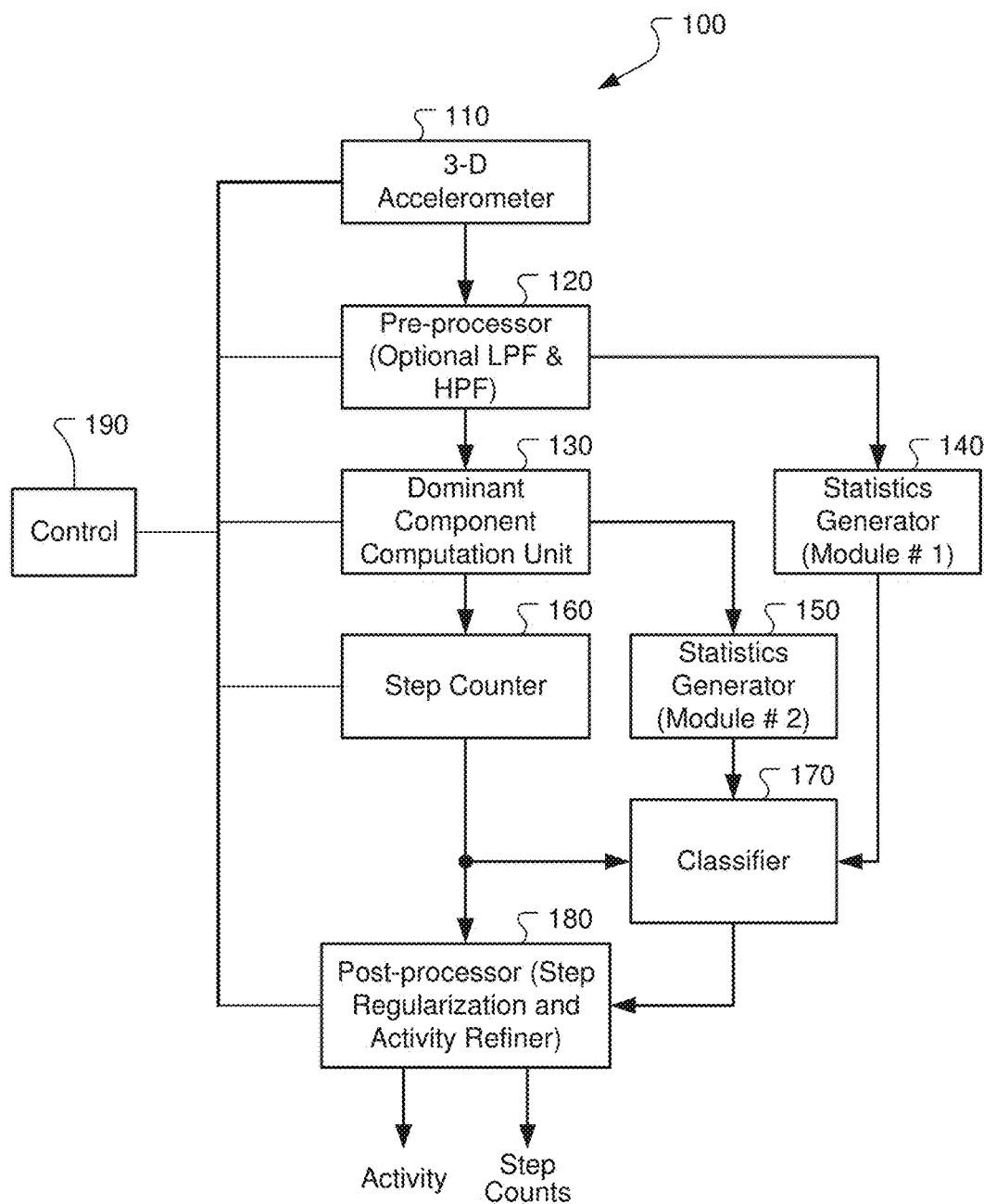
FIG. 1 illustrates an exemplary diagram of the tracking system for estimating activity and step count according to one embodiment of the present invention.

There are many different types of sensors that can be employed to collect activity data. For more refined results, the sensors should be used for a prolong period of time. Therefore, it is imperative that the sensors be lightweight and offer a reasonably long battery life. The embodiments described herein include a step counting device that contains one or more sensors. Generally speaking, micro electro-mechanical (MEMS) sensors are suitable to be included in the activity monitoring device. MEMS sensors are lightweight and use less energy to operate. Other types of sensors that are light weight and offer energy efficiency may also be suitable to be used in the activity monitoring device.

The systems and methods described herein provides sampling the data from sensors and processing the sampled data to calculate step count. Various embodiments described herein addresses several limitations and deficiencies currently being employed in activity monitoring and step counter products. First the processing of the sensors data is normally done in the time domain that may limit the accuracy and reliability of the result when the time domain sensor data are noisy or difficult to be classified into different activities in some cases. Another limitation of current step counting is that the optimization of step counting is normally done for one performance metric only. However, in real world applications it is desirable to optimize for multiple performance metrics (such as power consumption, accuracy, latency). Yet another typical limitation of the current activity tracking and step counting methods is using a fixed data sampling rate, which can lead to insufficient sampling for fast changing activities or unnecessary power consumption when rate is higher than needed.

In one embodiment, in conjunction with a processing system, an accelerometer is used to determine the activity and the step count of a user. If the accelerometer is placed at a fixed location and orientation on the body then a one-dimensional accelerometer is sufficient to determine the user activity that may include step counting. A 3-D accelerometer can be used to overcome the limitation of the fixed location and orientation. A 3-D accelerometer consists of three accelerometer elements, each sensing in perpendicular direction to the other two elements. In some embodiments, additional sensors such as gyros and magnetometers can also be used to improve the accuracy of the user's activity monitoring.

There exist a number of solutions that addresses the need of providing information to some extent. However, these solutions are not optimal for all performance metrics (such as accuracy, power consumption, latency, etc.) and are typically aimed at optimization of one metric based on the application requirement. Most of the solutions usually use time domain approaches in order to reduce computational requirements.

In accordance with one or more embodiments, a 3-D accelerometer is used in the step counter described herein to identify distinct user activities and also to collect information such as number of steps the user has walked irrespective of the orientation and location of the activity tracker on the body of the user. It should be noted that the term "user" used herein may also include non-human objects whose activities or movements need to be tracked. It should also be noted that the output of the activity tracker may also be used to derive auxiliary data such as calories expended, distance traveled, speed, jump height, etc.

FIG. 1 shows a top-level schematic of the activity tracking system 100 combining time domain and frequency domain processing. The activity tracking system 100 consists of a 3-D accelerometer 110 and one or more signal processing modules to process the accelerometer data and to determine the activity of a user who is using the activity tracking system 100. In one embodiment, a classifier 170 is included to process the pre-processed data based on the output of one or more statistics generators 140, 150 to determine the user's activity. In other embodiments, the classifier 170 may be placed (or implemented) in an external device such as a mobile phone device. The classifier 170, if implemented in an external device, may communicate with the activity tracking system 100 to collect the 3-d accelerometer data (either raw or after pre-processing in the activity tracking system 100) and send the activity classification back to the activity tracking system 100.

The 3-D accelerometer 110 provides data samples along X-axis, Y-axis and Z-axis at a pre-selected and optionally configurable sampling rate to a pre-processor 120. The sampling rate may also be adjusted dynamically based on user activity. For example, if no activity or slow changing activities are observed, the sampling rate may be reduced. It may be noted that a reduced sampling rate may result in power saving.

The pre-processor 120 normalizes the data provided by the 3-D accelerometer 110. The pre-processing may include removing gravitational component (e.g., acceleration due to gravity, equal to 9.8 m/s$^2$). In other embodiments, the pre-processing may also include removing noise from the data received from the 3-D accelerometer 110. In some embodiments, a filtering operation follows the normalization process to reduce the noise of the signal. In particular, a direct current (DC) notch filter is used to remove, if necessary, the DC component present in each of the three axis accelerometer data. A low pass filter (LPF) can also be used to suppress high frequency components, as most of the activity information is present in frequency components below 5 Hz while high frequency components typically correspond to noise. A low order LPF is used to reduce computational requirements. In some embodiments, the pre-processor 120 may include a low pass filter (LPF). In other embodiments, the pre-processor 120 may include a high pass filter (HPF). And in some other embodiments, both LPF and HPF may be included. The pre-processor 120 may also perform calibration of the input data based on a preset criteria.

A dominant component computation unit 130 is included to determine a dominant component in the data provided by the 3-D accelerometer 110. The determination of the dominant component may include computing a vertical and a horizontal component in the data received from the 3-D accelerometer 110, and then determining which one of the horizontal and the vertical components is the dominant component. For example and for the ease of understanding only, if the activity tracking system 100 is mounted in a shoe, the horizontal component may be the dominant data whereas if the activity tracking system 100 is mounted on the arm, the vertical component may be the dominant data for the purpose of determining the activity and counting steps.

Typically, the dominant component computation is needed because the sensor position and/or orientation is not known. In one embodiment, the data received from the 3-D accelerometer 110 is projected along vertical axis and horizontal plane. This projection makes the data received from the 3-D accelerometer 110 independent of the sensor orientation.

One or more statistics generator modules 140, 150 may be included to extract statistical attributes from previous data captured from the dominant component computation unit 130 and the pre-processor 120. The statistics data may also be inputted to the statistics generators 140, 150 from an external source as for example, the activity tracking system 100 may be preconfigured with sample statistical data. Over the period of use, the externally inputted statistical data may be refined based on the data collected from the pre-processor 120. In some embodiments, the functionality of the two statistics generators 140, 150 may be combined in one single unit.

In some embodiments, the activity detection is based on a time domain sensor data, a frequency domain transformed data, or both. According to one embodiment, the activity is determined based on features derived from time domain sensor data including a vertical component or a horizontal component. In another embodiment, the activity detection is based on frequency domain transformed data. In some embodiments, time domain (TD) and frequency domain (FD) data processing can also be combined for more accurate activity tracking. It should be noted that at least some of the modules described herein may be implemented in software or hardware.

In some embodiments, a sample data is selected in the analog output of the 3-D accelerometer 110. For example, a sample may include a data within a selected time slot or a selected length. The sampled data may then be split into blocks of sub-samples (e.g., example 3 or 4 seconds long snapshots). A dominant component is determined in the sampled blocks. The dominant component may be Horizontal or Vertical component. One or more attributes or features are computed in each of the sampled blocks. Examples of the extraction of attributes may include computing mean, variance, and energy of the time domain signal. In another example, the extraction of attributes may include one or more of computing mean, variance, signal energy of the previously determined dominant component. In other examples, peak value, location, sub-band energy of the frequency domain signal may be computed. Computing features or attributes on the dominant component in the output of the 3-D accelerometer is beneficial because calculations on the dominant component to determine an activity provide better identification of the activity compared to performing the calculations on the raw data provided by the 3-D accelerometer 110 because the orientation and/or placement of the 3-D accelerometer 110 may skew activity detection without first finding the dominant component in the raw data provided by the 3-D accelerometer.

The statistics generators 140 or 150 can be used to perform frequency domain transformation and generate statistical attributes based on the frequency domain transformed data. The classifier 170 determines the current activity status based on the generated statistical attributes. In some embodiments, the step counter 160 uses the output of the dominant component unit 130 to estimate step count. Also in some embodiments, a post-processor 180 may be used to further regularize the estimated step count and refine the activity status calculated by the classifier 170. In some embodiments, the statistics generators 140 and 150 may be combined in one module. In one embodiment, the statistics generators 140 and 150 may perform frequency domain transformation on the data received from the pre-processor 120 or the dominant component computation unit 130.

Step counter module 160 calculates the steps based on the vertical component V or the horizontal component H. It involves frequency-domain and time-domain processing. The vertical/horizontal component is first transformed to frequency-domain.

In an example, the classifier 170 and the step counter 160 operate independently on the preprocessed 3-D accelerometer data. Hence, in some instances the outputs of the classifier 170 and the step counter 160 may be in conflict. For example, the classifier 170 could indicate that the user is idle while the step counter 160 could output non-zero number of steps. This situation may occur when the step counter 160 does not use a minimum threshold to check for the signal level. Therefore, post-processing is performed to combine the information from the classifier 170 and the step counter 160 to minimize errors. In this example, the post-processing steps use information about normal human behavior to refine the output.

Figure 5:
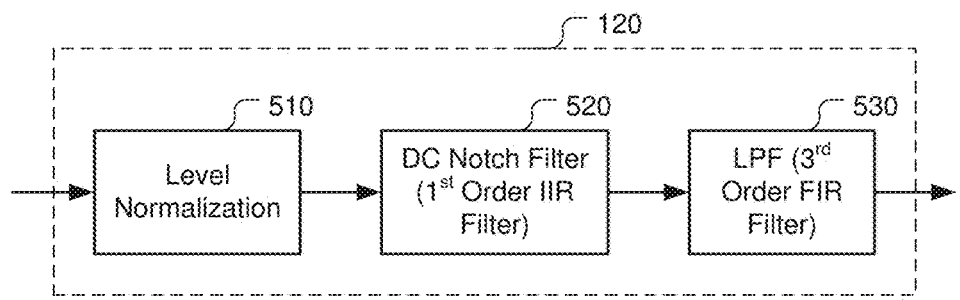
FIG. 5 illustrates an exemplary block diagram of the pre-processor.

In some embodiments, to obtain the representative captured data, a data logging exercise is performed with several users performing multiple activities such as walking, running, sitting, standing, walking up/down stairs, jumping, etc. The representative captured data is pre-processed by the method as shown in FIG. 5 and the attributes are extracted from the 3-D data obtained from generate statistics modules (#1 and #2), and the step counter module 160 as shown in FIG. 1. The attributes together with the class information are stored in a database. The attributes derived from the training data are analyzed to check the suitability of each attribute for reliably identifying the class.

WEKA (Waikato environment for knowledge analysis) software package can be used to derive the classifier. The software package provides multiple classifier options and the appropriate classifier can be selected based on the confusion matrix output, which is a well-known tool in WEKA. Confusion matrix is a specific table layout that allows visualization of the performance of an algorithm. The confusion matrix makes it easy to see if the system is reliably classifying the different classes.

In the present invention, a variation of the nearest neighbor classifier is used to distinguish different activities. The first step in this method is to analyze the range of each attribute for all the activities. An attribute is considered as a good attribute for a classifier if there is no overlap in attribute values among different activities. Usually this condition is difficult to satisfy, as there will be always some outliers (or samples) that would tend to blur the gap between any two activities. Given this fact, the attributes with the minimum overlap on value ranges of all activities are selected as good attributes.

The control module 190 is used for system initialization, configuration, monitoring and a plurality of control functions. The control module 190 provides control signals or commands to one or more processing modules that are depicted in FIG. 1. The control module 190 may also provide data processing support to one or more processing modules depicted in FIG. 1. The control module 190 can be implemented based on a CPU (central processing unit), one or more microcontroller, individual embedded controllers associated with processing modules, or a combination thereof. In some embodiment, the control module 190 may implemented using logic circuits for performing predefined specific operations. The control module 190 may also be programmable via software, firmware or micro codes.

The control module 190 can be configured to manage reliability, latency and battery life trade-offs. Control algorithm requires a number of parameters that can be configured automatically depending on certain operating conditions. To improve the performance, the control module 190 may be programmed to perform additional processing based on the position of the accelerometer 110. For example, the control module 190 may change some of the thresholds used in the classifier 170 and the step counter 160 based on the position of the 3-D accelerometer 110.

In some embodiments, the control module 190 can also be used to control the operation of the 3-D accelerometer. Typically, the 3-D accelerometer provides analog data, which is sampled along X-axis, Y-axis and Z-axis at a pre-defined sampling rate, preferably using an analog to digital converter, to produce digital output. The sampling rate can be adjusted upward or downward dynamically based on detected or predicted activity. For example, when slow changes in activity are detected, the sampling rate of the analog to digital converter may be reduced, to save battery power without compromising the accuracy of the results. The sample rate is increased back to the original rate when enhanced activity is detected.

In one embodiment, the activity tracking system 100 may include a switch which is configured to trigger a "sleep mode". When the activity tracking system 100 is transitioned into the "sleep mode", the sampling rate is reduced to a predefined low value. In another embodiment, the control module 190 may be configured to transition the activity tracking system 100 in the "sleep mode" based on the output of at least one of the step counter 160 and the classifier 170.

Figure 2:
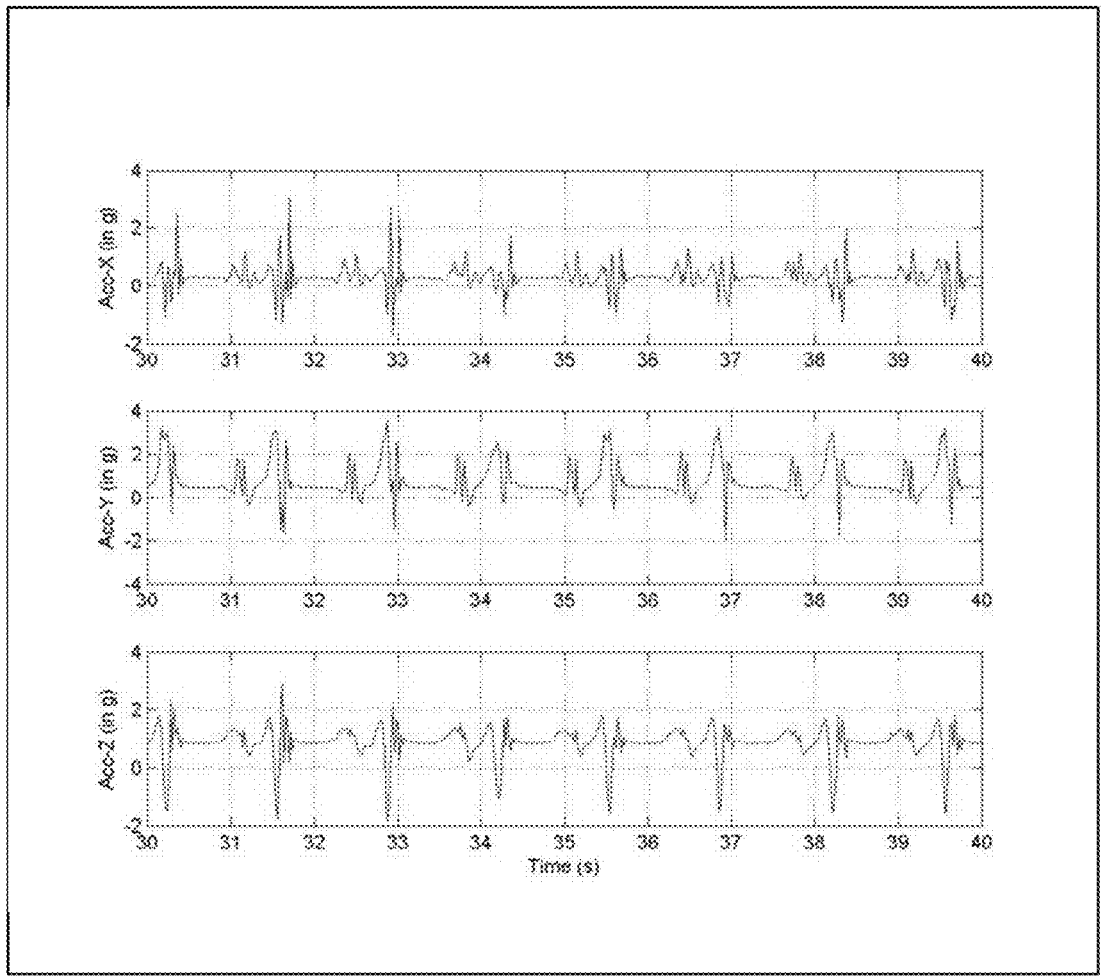
FIG. 2 illustrates an example of 3-D accelerometer data from a sensor placed on one shoe for walking activity.
Figure 3:
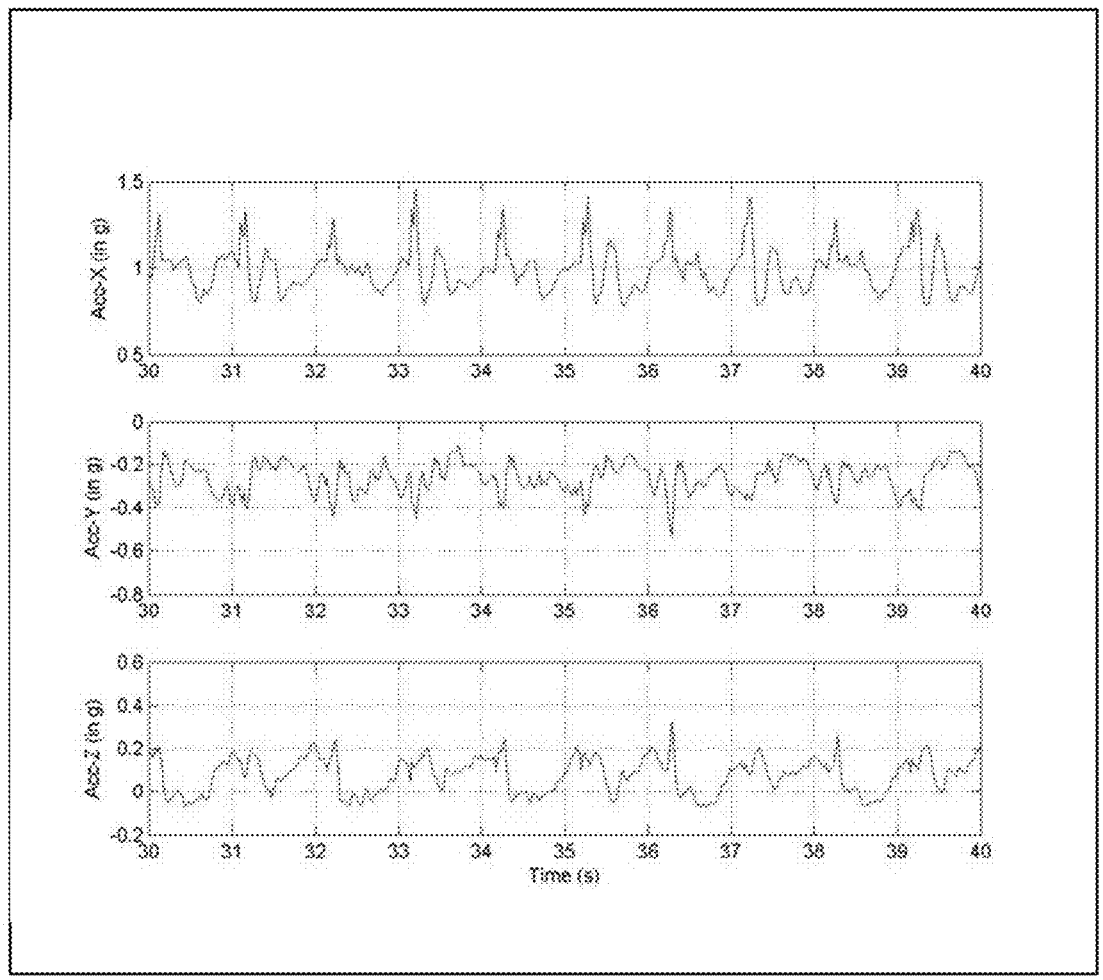
FIG. 3 illustrates an example of 3-D accelerometer data from a sensor placed on one wrist for walking activity.
Figure 4:
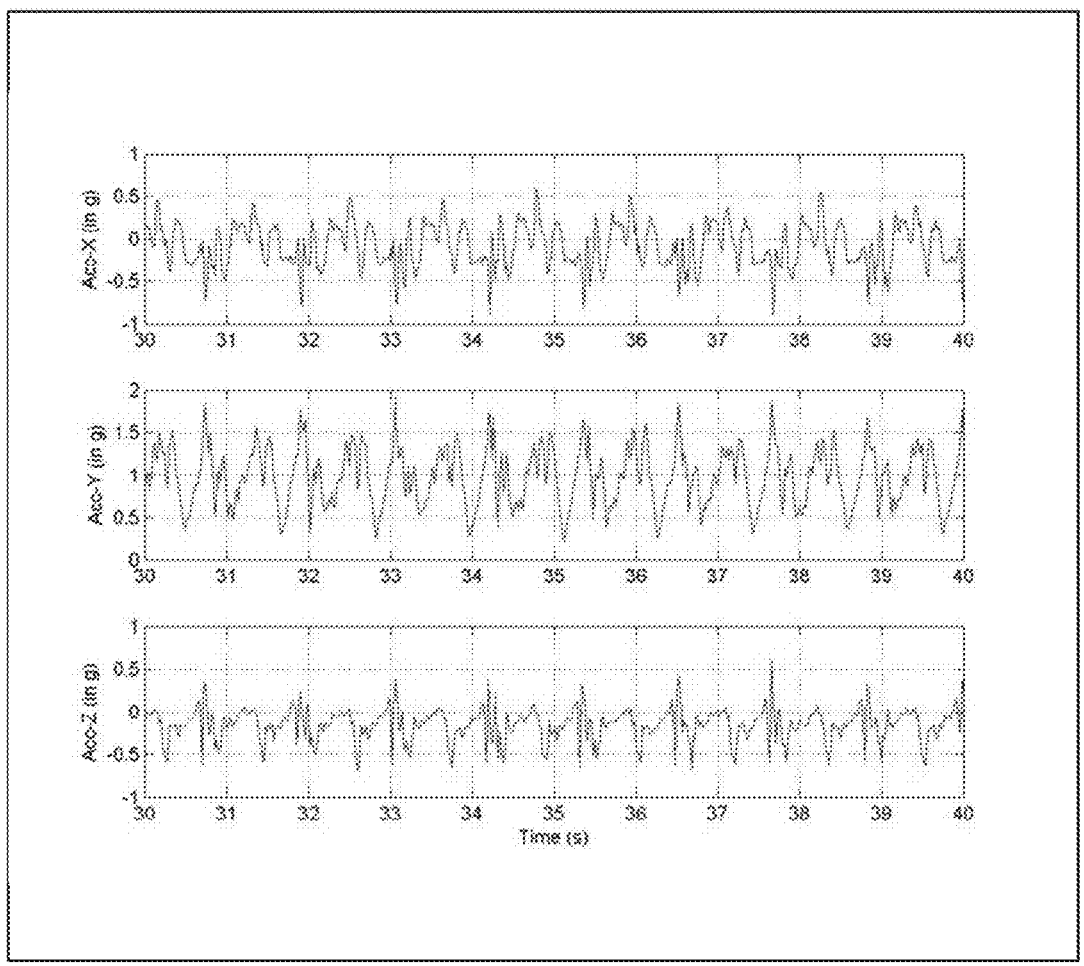
FIG. 4 illustrates an example of 3-D accelerometer data from a sensor placed on the waist for walking activity.

For the purpose of easy understanding of the systems and method described herein, the following paragraphs uses non-limiting examples. For activity tracking, the 3-D accelerometer 110 can be placed on one shoe, one wrist, or the waist of the user, etc. FIG. 2, FIG. 3 and FIG. 4 show snapshots of the 3-D accelerometer data in the same 10 seconds with different sensor placements for the same user. Each snapshot of 3-D accelerometer data is from one sensor used for tracking user activity. FIG. 2 illustrates a snapshot of 10 seconds 3-D data from the sensor placed on one shoe. FIG. 3 shows the data from the sensor placed on one wrist and FIG. 4 shows the data from the sensor placed on the waist of the user. As can be observed, there is a significant variation in the data from one sensor location to another sensor location, although the overall trends seem to be similar.

FIG. 5 shows an example of pre-processor 120. The accelerometer data is normalized by level normalization 510. Then, a DC notch filter 520 and a LPF 530 process the normalized signal. In this example, a first order IIR (infinite impulse response) filter is used as a DC notch filter and a third order FIR (finite impulse response) filter is used as the LPF 530.

Dominant component computation 130 is used to extract step information, such as vertical and horizontal components for step counting. As the sensor position is not known a priori, the 3-D data is combined in order to extract the step information. According to one embodiment of the present invention, the 3-D data is projected along vertical axis and horizontal axis for calculating the vertical and horizontal components. This will make the data independent of the sensor orientation and therefore can be used with different sensor placement options by simple parameter tuning.

Data $\overline{A}=(A_x, A_y, A_z)$ denotes the pre-processed 3-D accelerometer data at a given sample instant.

The mean along the three axes $\overline{m}$ is given by:

$$\overline{m}=(m_x,m_y,m_z).$$

Then the dynamic component of the accelerometer data $\overline{D}$ can be generated using the following equation:

$$\overline{D}=(A_x-m_x,A_y-m_y,A_z-m_z).$$

The projection of the dynamic component along the vertical component direction is given by the vector inner product of $\overline{D}$ and $\overline{m}$, which is described by:

$$V = \overline{D} \cdot \frac{\overline{m}}{\|\overline{m}\|}.$$

The horizontal component can be obtained by projecting the dynamic component along the horizontal component direction, which can be described as:

$$H=\|\overline{D}-V\overline{m}\|.$$

For normal activities, the estimate of vertical component V, which is independent of sensor orientation, includes useful information and can be used to determine the step count. In this case, the vertical component is taken as the dominant component. In some instances, particularly for certain sensor positions, the horizontal component (also referred to as orthogonal component) rather than the vertical component will provide more useful information. Then the horizontal component is considered to be the dominant component.

Figure 6:
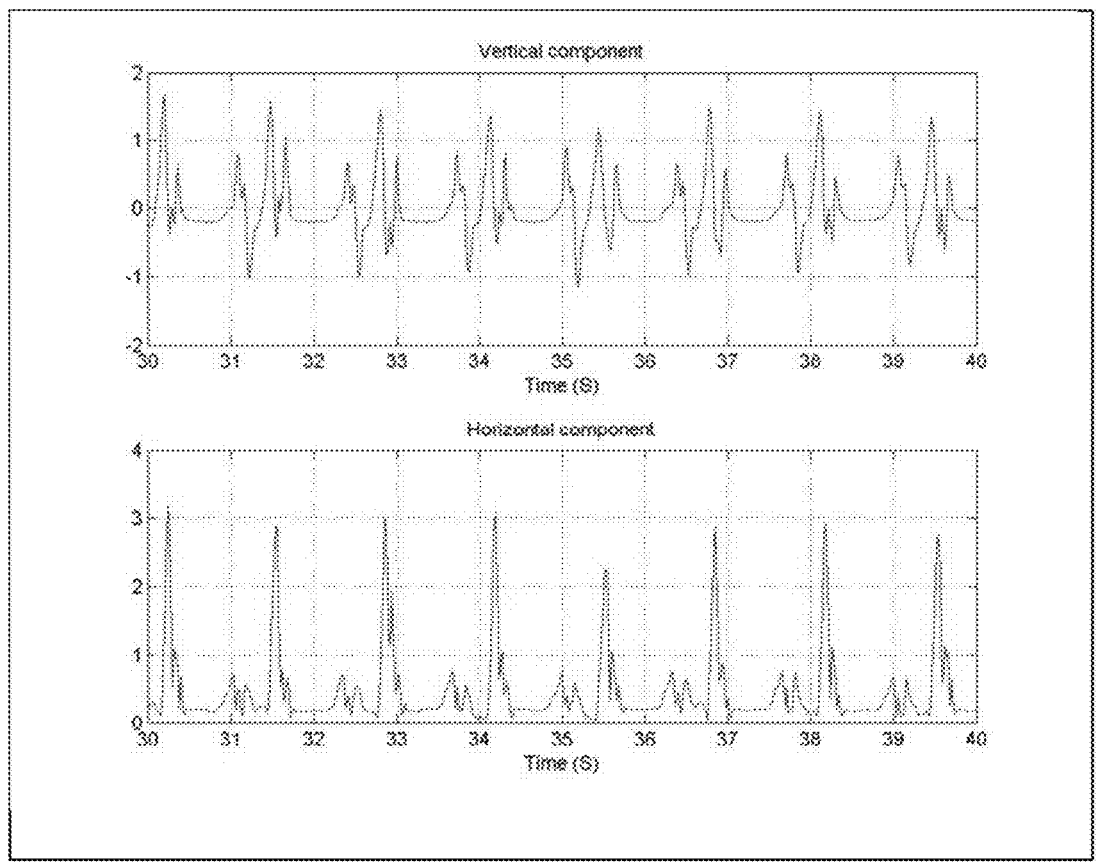
FIG. 6 illustrates an example of vertical and horizontal component estimated from the 3-D accelerometer data obtained by the sensor placed on the shoe.
Figure 7:
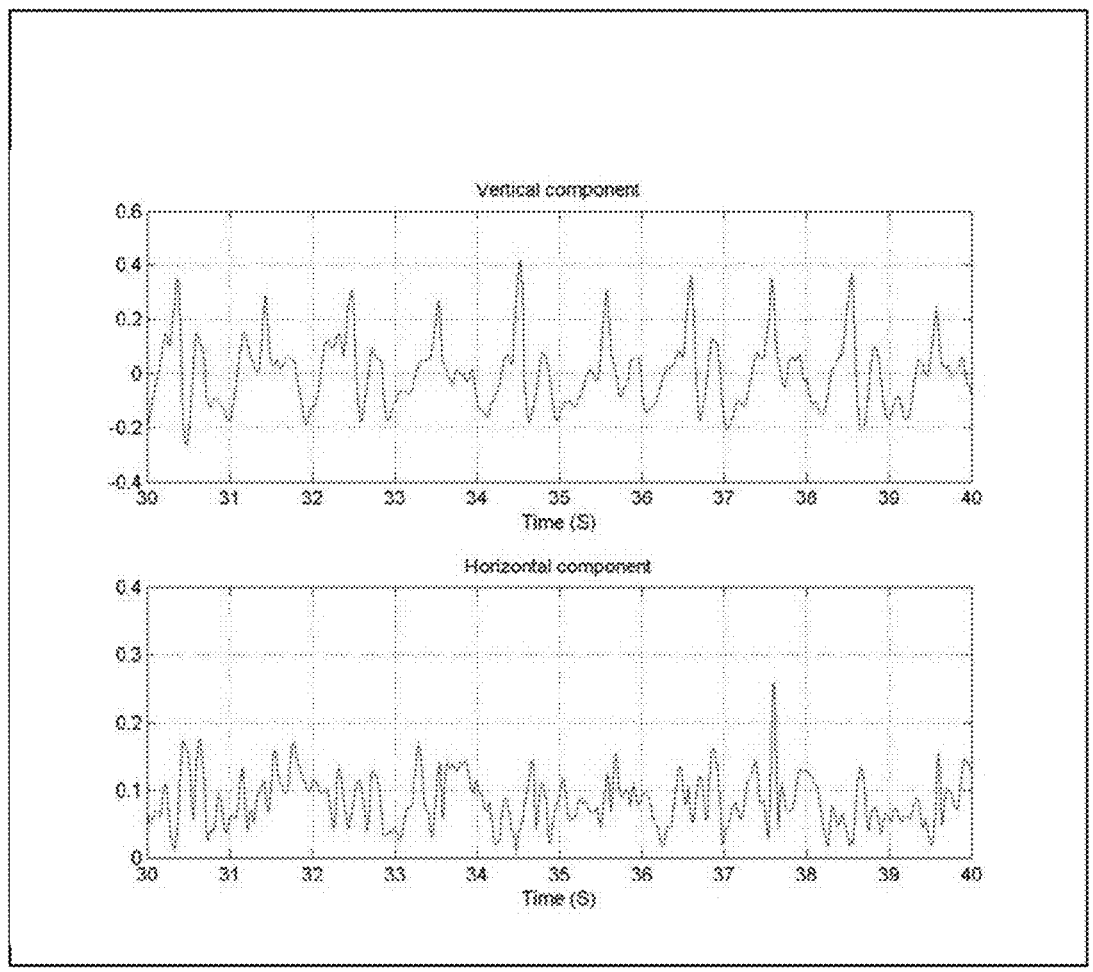
FIG. 7 illustrates an example of vertical and horizontal component estimated from the 3-D accelerometer data obtained by the sensor placed on the wrist.
Figure 8:
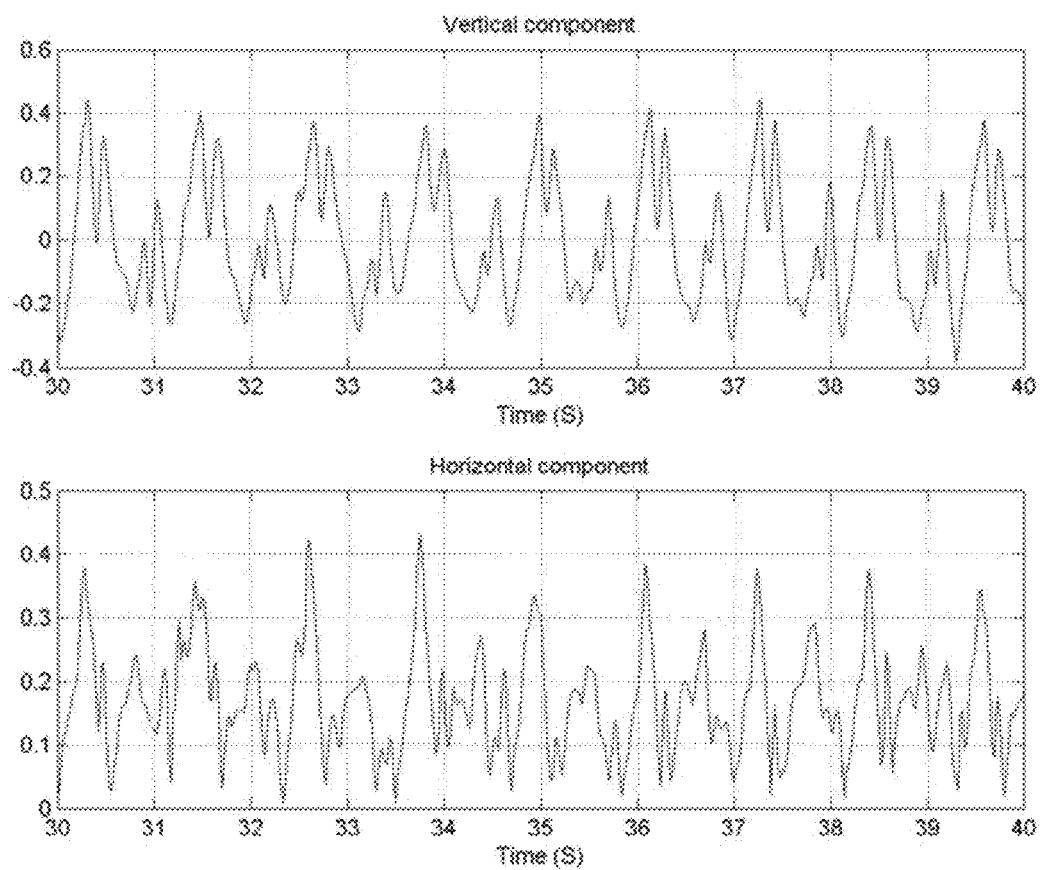
FIG. 8 illustrates an example of vertical and horizontal component estimated from the 3-D accelerometer data obtained by the sensor placed on the waist.

FIG. 6, FIG. 7 and FIG. 8 illustrate the vertical and horizontal component estimates from the 3-D accelerometer data shown in FIG. 2, FIG. 3 and FIG. 4 respectively. It can be observed from the plots that when the sensor is placed on one shoe the horizontal component has well-defined pattern compared to the vertical component. On the other hand, when the sensor is placed either on one wrist or the waist, the vertical component has well-defined pattern compared to the horizontal component.

The output of each sensor represents a sampled version of the acceleration along the three orthogonal axes. In order to determine the user activity based on the 3D accelerometer data, some attributes (or features) are derived from this data. The attributes help in compactly representing the data and as a result it is easier or manageable to generate the classifier based on the training data. Also, it is more computationally efficient to use the attributes from the test data, compared to using the raw data, to determine the user activity and step count.

According to the embodiment, the activity detection and step counting are based on the statistical attributes derived from the time domain sensor data. The attributes derived from the time domain sensor data are selected from three sets. One set is the attributes derived from the individual axis accelerometer data; another set is the attributes calculated from the combined accelerometer data; and the third set is the attributes derived from the vertical and horizontal components.

A number of time domain attributes are extracted from the 3D accelerometer data. Data A(n) denotes the combined accelerometer data, which is described by:

$$A(n)=|A_x(n)|+|A_y(n)|+|A_z(n)|.$$

The attributes derived from the individual axis accelerometer data are described by the following formulas. The mean $m_k$, variance $var_k$, peak $p_k$ and peak to average ratio $PAR_k$ of the individual axis accelerometer data are described by:

$$m_k = \frac{1}{N}\sum_{n=1}^{N} A_k(n),$$

$$var_k = \frac{1}{N}\sum_{n=1}^{N} (A_k(n)-m_k)^2,$$

$$p_k = \max_{1 \le n \le N}(A_k(n)), \text{ and}$$

$$PAR_k = \frac{p_k}{m_k}.$$

where k can be used to denote x, y or z axis. The mean, variance, peak and peak to average ratio of magnitudes of the individual axis accelerometer data are given by the following formulas respectively:

$$\overline{m}_k = \frac{1}{N}\sum_{n=1}^{N}|A_k(n)|,$$

$$\overline{var}_k = \frac{1}{N}\sum_{n=1}^{N}(|A_k(n)| - \overline{m}_k)^2,$$

$$\overline{p}_k = \max_{1 \le n \le N}(|A_k(n)|) \text{ and}$$

$$\overline{par}_k = \frac{\overline{p}_k}{\overline{m}_k}.$$

The attributes derived from the combined accelerometer data are computed based on the combined data of the three axes. The mean, variance, peak and peak to average ratio of combined accelerometer data are denoted as m̈, v̈ar, p̈ and PÄR respectively and given by:

$$\ddot{m} = \frac{1}{N}\sum_{n=1}^{N}A(n),$$

$$\ddot{var} = \frac{1}{N}\sum_{n=1}^{N}(A(n) - \ddot{m})^2,$$

$$\ddot{p} = \max_{1 \le n \le N}(A(n)), \text{ and}$$

$$P\ddot{A}R = \frac{\ddot{p}}{\ddot{m}}.$$

The time domain energy of the combined accelerometer data is described by:

$$E_{TD} = \frac{1}{N}\sum_{n=1}^{N}(A(n))^2.$$

The attributes derived from the vertical and horizontal components are computed by the following formulas. The mean of vertical component is simply an average value of vertical component described by:

$$m_v = \frac{1}{N}\sum_{n=1}^{N}V(n).$$

The mean of horizontal component is an average value of horizontal component described by:

$$m_h = \frac{1}{N}\sum_{n=1}^{N}H(n).$$

The variance of vertical component $var_v$ or the variance of horizontal component $var_h$ is an average value of the square of the difference between the vertical or horizontal component and the corresponding mean described by:

$$var_v = \frac{1}{N}\sum_{n=1}^{N}(V(n) - m_v)^2, \text{ and}$$

$$var_h = \frac{1}{N}\sum_{n=1}^{N}(H(n) - m_h)^2.$$

In another embodiment, frequency domain attributes are used to detect activities. Frequency domain attributes are calculated based on the frequency domain transformation $\mathcal{A}$. When the data $A(n)$ is used in the frequency domain module, the frequency domain transformation is described by:

$$\mathcal{A}(k) = DFT(A(n)) = \frac{1}{N}\sum_{n=1}^{N}A(n)e^{-j2\pi k(n-1)/N},$$

where k=0 to N−1. The attributes derived from frequency domain transformed data include the peak of frequency domain transformed data, the location of the peak of the frequency domain transformed data and the sub-band frequency domain energy. The peak of frequency domain transformed data is the max value of the frequency domain transformation described by $$P = \max_{1 \le k \le N}(\mathcal{A}(k))$$

The location of the peak of the frequency domain transformed data is given by:

$$L = (\mathcal{A}(k) = P)_{k=1 \text{ to } N/2}$$

The sub-band frequency domain energy is a sum value of the squared data described by:

$$E_{FD} = \Sigma_{k=k_{init}}^{k=k_{final}}(\mathcal{A}(k))^2,$$

where $k_{init}$ and $k_{final}$ represents the initial and final frequency components of interest.

In another embodiment, the vertical component V(n) or the horizontal component H(n) is used to extract statistical attributes instead of A(n) in the frequency domain module. Then, the frequency domain attributes are calculated by using V(n) or H(n).

Figure 9:
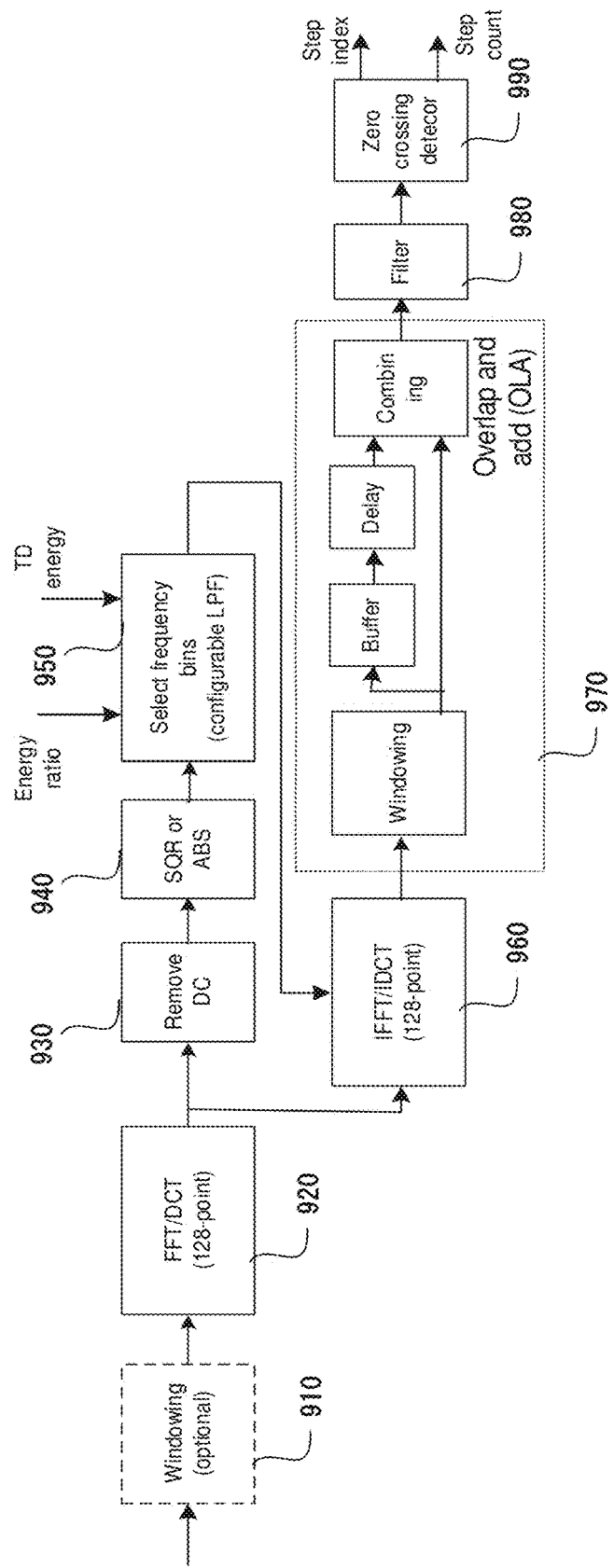
FIG. 9 illustrates a schematic of a Frequency Domain (FD) processing unit in the step counter in accordance with one or more embodiments.

FIG. 9 shows the block diagram 900 of the operations of the step counter module 160. The step counter module 160 receives the vertical/horizontal component computed from the pre-processed 3D accelerometer data. Alternately, 3D accelerometer data without pre-processing can also be used as the input to the step counter module 160. In one example, the magnitude of the 3D accelerometer data is computed as $\sqrt{A_x^2 + A_y^2 + A_z^2}$ and input to the step counter 160. An optional windowing function 910 can be used to process the input data, which is then fed to a Fast Fourier Transform (FFT) module 920. Alternately, a Discrete Cosine Transform (DCT) can also be used instead of FFT to reduce computational requirements. The FFT module 920 provides a computationally efficient implementation of the Discrete Fourier Transform (DFT). The FFT size is configurable or programmable and can be configured via the sampling rate of the incoming data. For example, for 50 Hz sampled data a 128-point FFT may be used. The DC component in the FFT output contains static component (usually acceleration due to gravity) and is therefore removed in a DC removal module 930. These steps are represented mathematically as shown below:

$$\mathcal{V}(k) = DFT(V(n)) = \frac{1}{N}\sum_{n=0}^{N-1} V(n)e^{-j2\pi kn/N}$$

$$\mathcal{V}(k_{max}) = 0, \text{ where } k_{max} = \frac{\max}{k \in (0, N-1)} |\mathcal{V}(k)|$$

Figure 10A:
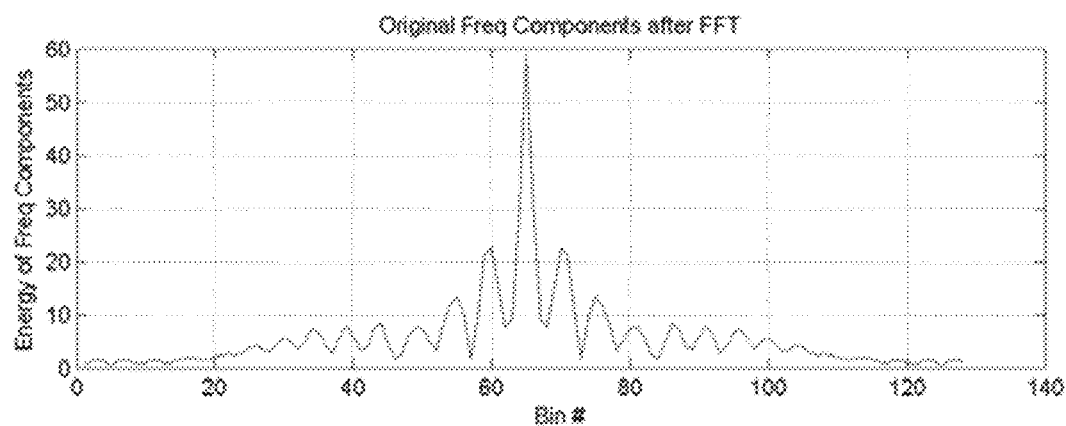
FIG. 10A shows an output of Fast Fourier Transform $(v(k))$ module.
Figure 10B:
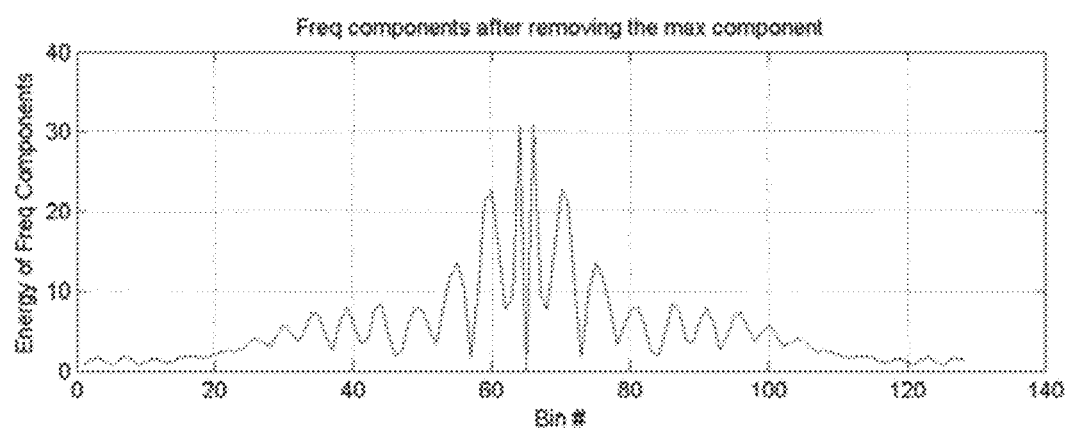
FIG. 10B shows an output of FFT with $v(k_{max})=0$.

FIG. 10A shows the output of FFT V(k) and FIG. 10B shows the FFT output with V $(k)_{max}$=0 for a sample snapshot.

It may be noted that a user wearing the activity tracking system 100 may not be moving at a same frequency in a selected period of time. Therefore, in one embodiment, based on an input energy threshold, activity frequencies that include energy greater (or at least equal to) than the input energy threshold are selected as follows. The FFT output is then squared in the SQR module 940 and processed to select the significant frequency bins in a configurable low pass filter (LPF) 950. First the total energy is calculated as $$E_{Total} = \sum_{k=1}^{\frac{N_{FFT}}{2}-1} \mathcal{V}(k)^2$$

Then the first bin index is determined that meets the condition $$\sum_{k=1}^{k_{min}} \mathcal{V}(k)^2 \geq EnergyRatio * E_{Total}$$

Where EnergyRatio is a configurable parameter and can be automatically set by the control block. A new vector $\overline{v}$ is formed retaining only the bins less than $k_{min}$ from v. The remaining bins are made zero. This vector $\overline{v}$ is transformed back into time domain by performing IFFT operation 960 as shown below.

$$\overline{V}(n) = IDFT(\overline{\mathcal{V}}(k)) = \frac{1}{N}\sum_{k=0}^{N-1} \overline{\mathcal{V}}(k)e^{j2\pi kn/N}, \text{ where } n = 0 \text{ to } N-1$$

Figure 11:
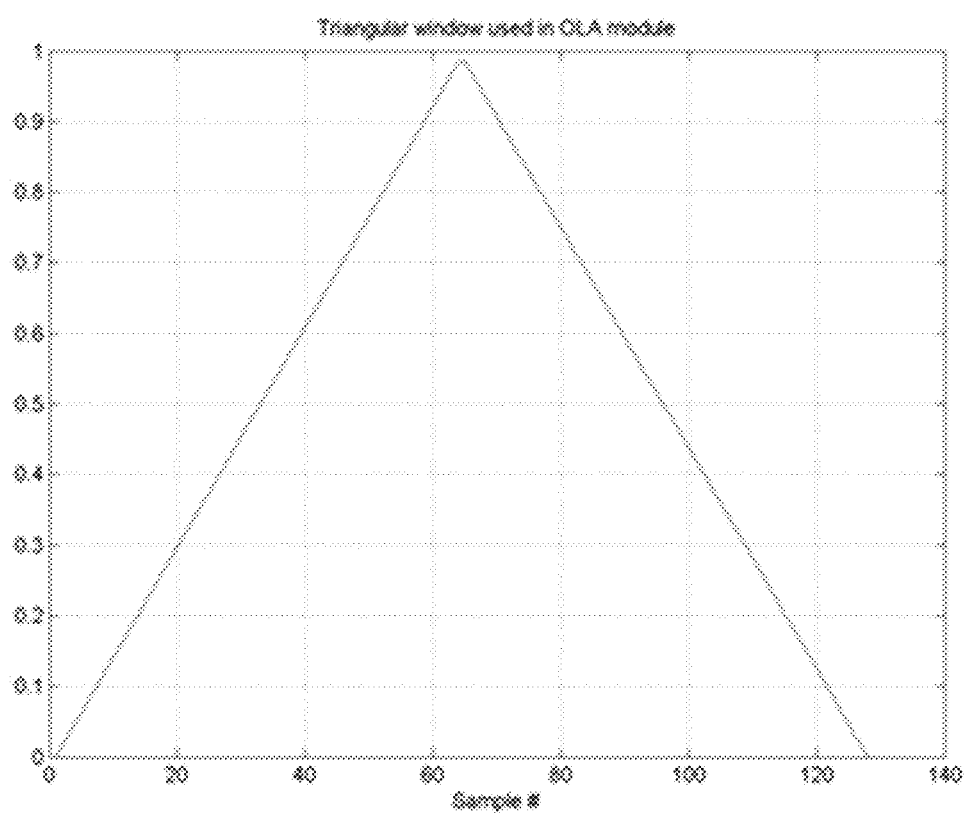
FIG. 11 shows a triangular window used in an overlap and add method.
Figure 12:
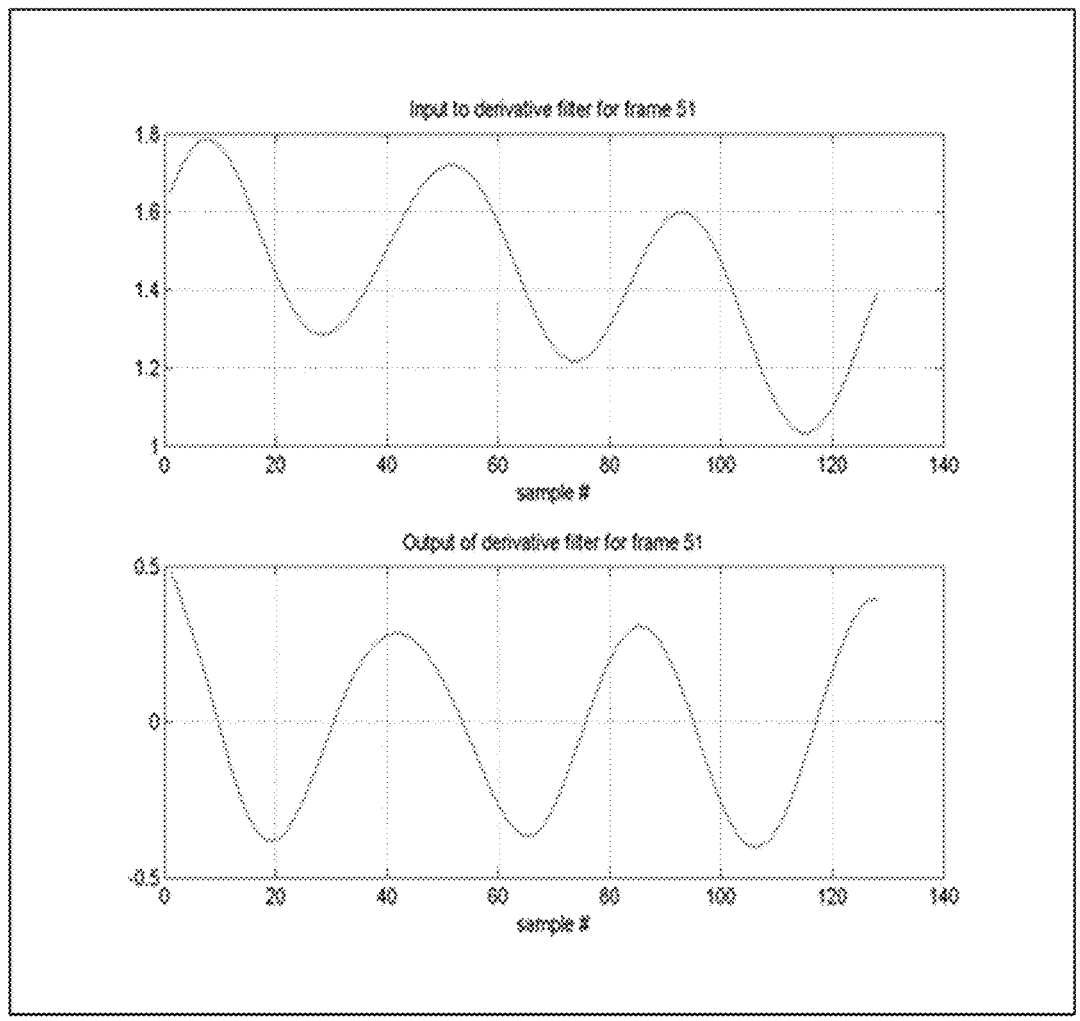
FIG. 12 shows a snapshot of the input and output of the derivative filter for running activity.

Since only a small fraction of components of $\overline{v}$ are non-zero, a sparse IFFT routine can be used to reduce computations. Overlap and add (OLA) module 970 is used to combine two adjacent blocks of IFFT output. Different window options, for example the triangular window shows in FIG. 11, can be used within the OLA module 970 depending on performance and computational requirements. The output of the OLA module 970 is processed using a derivative filter 980 and a zero crossing detector 990 to determine step instances. The total number of step instances provide the step count information. As an example, FIG. 12 shows a snapshot of the input and output of the derivative filter 980 for running activity.

FFT/IFFT based step counting algorithm smoothes the baseline waveform like a cosine shape thus enabling to count steps in an easy manner. However, there exists false alarm especially in idle activity status, for example, when the user is sitting or standing, the user's body would not be static and accelerometer sensor may capture signals with magnitude fluctuation. On the other hand, in some case of irregular movement in active status, there is obvious error in step counter.

Typically, the classifier 170 and the step counter 160 operate independently on the accelerometer data. Hence, in some instances the outputs of these two modules may be in conflict. For example, the classifier 170 may indicate that the user is idle while the step counter 160 may output non-zero number of steps. This may happen as the step counter 160 does not use a minimum threshold to check for the signal level. Also, the classifier 160 is not accurate in all activity scenarios. Post-processing steps may be employed to combine the information from both these modules to minimize errors. These post processing steps may use information about normal human behavior to refine the output.

For example, to remove false steps when activity is idle, if time domain (TD) energy is significantly low (i.e. less than the lowest active state energy) then it may be assumed that this is indeed idle state and therefore force the number of steps to 0. In another example, when activity is active, an assumption may be made that the fastest step rate is about 5 steps per second. If step gap between two adjacent step instances is less than 0.2 second then it may be considered as a false step and may be removed. In some example, the process of removing false steps may be continued successively for all the steps instances provided by the step counter 160.

Also, weighted average of step duration over last few steps may be computed and the computed parameter is used to compare the current step duration. If the current step duration is outside a window of weighted average then it is noted either as a false step or a missed step.

Activity classification may also be refined using the output of the step counter 160. If TD energy is reasonable for active state. In cases where a user is slow walking, the classifier 170 may mis-classify the activity as idle. If the step count is small so that it corresponds to slow walking activity then it is assumed that the step count information is correct. The classifier 170 output for the previous two frames (about 5 sec total duration) is checked and if the activity for the two frames was walking then the activity may be reclassified for the current frame as walking.

There may be some instances where the classifier 170 may output the state as active (walking), while the step count is zero. In this case, it may be assumed that the step count information is correct and the activity may be reclassified to idle. The activity tracking system 100 may be configured to make similar adjustments through programming instructions or configuration data.

Figure 13:
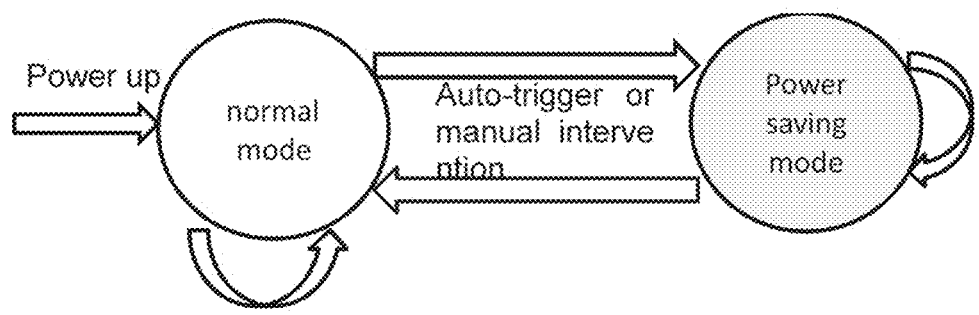
FIG. 13 shows a sample schematic of a finite state machine used for collaboration of a plurality of modules of a step counter system.

In the activity tracking system 100, the basic operation modes include normal mode, low power mode and sleep mode. In normal mode, accelerometer sensor, microcontroller (MCU) are operating in high performance state so as to obtain the most reliable activity status tracking, step counting performance and possibly timely information exchange with other devices, i.e., mobile phone, tablet and so on. Low power mode means all or parts of modules operate with low power consumption which is a tradeoff between performance and power consumption. In sleep mode, many modules of the activity tracking system 100 are turned off to achieve lowest power consumption, and meanwhile the activity tracking system 100 may be waked up upon a request. The transition between the normal mode and low power mode should fast enough and should avoid dead lock which requires deliberate design of finite state machine (FSM) as shown in FIG. 13.

One of the primary functions of the FSM is to ensure collaboration among various modules of the activity tracking system 100. The FSM includes two basic states, "normal" and "power-saving". The "power-saving" mode may include some sub-states, such as, low-power working, and different levels of sleep modes. Note that the transitions between each state and/or each sub-state are triggered by inherent interruption signals based on signal level detection. In addition, these transitions can also be controlled manually according to specific application requirements. In some embodiments, a long advertising interval may be used to reduce average current and low data transmission rate to reduce the peak current which results in increased battery life.

Figure 14:
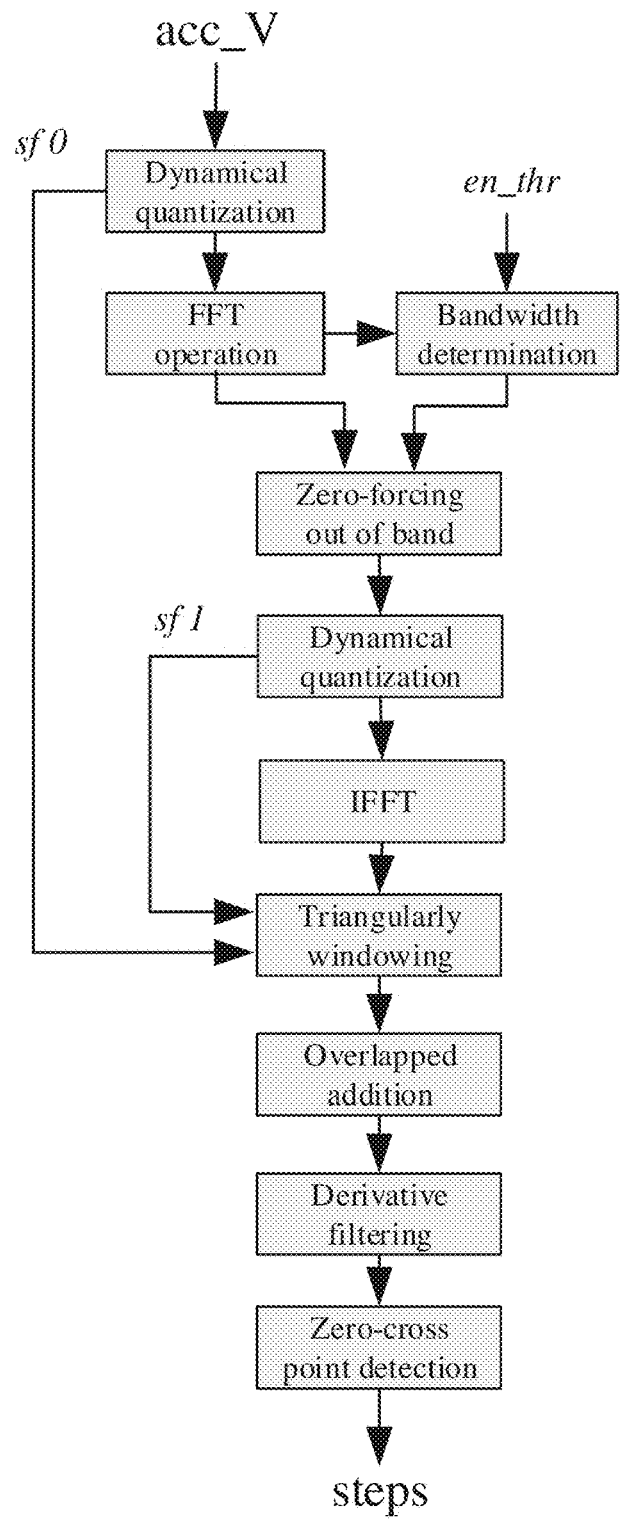
FIG. 14 shows a flow diagram of the operations performed by the FD processing module in the step counter.

FIG. 14 illustrates a sample signal flow in the step counter 160. Acc_V is the accelerometer derived data, which may include the 3-d accelerometer data or the 3-D accelerometer data after pre-processing as described above. Input parameter en_thr is the pre-defined threshold in energy detection. If the summation of energy at interval from bin −k to k is no less than the product of total energy by en_thr, an interval [−k, k] is obtained. The bandwidth of interest is [−k, k] with minimum value of integer k. In one example, in each overlapped addition operation, a half frame signal is obtained by adding the first half signal in current frame by the second half signal in the previous frame. In one example, derivative filter of coefficients [2,1,0,−1,−2] may be chosen which is convolution of [1,−1] and [2, 3, 3, 2], where [1,−1] accounts for derivation and [2, 3, 3, 2] is a low-pass filter to smooth the fluctuation in derivation signal. As shown, control signals sf 0 and sf 1 are used in the triangularly windowing module.

The step counter 160 may be implemented in hardware or software. If implemented in software, the programming instructions are executed by a processor of the activity tracking system 100. In some embodiments, the maximum frequency bin is found based on a pre-defined energy threshold. This way a frequency interval that is symmetric around zero frequency is obtained. All components outside of this frequency interval are set to be zero which is mathematically equivalent to ideal low-pass filtering. The resulting low pass signal is then transformed to time-domain and windowed by triangle window and added to previous half frame signal since we introduce half frame overlap between two adjacent frames. The aim of windowing is to avoid the discontinuity between two frames. Low-pass filtered time-domain signal is passed through derivative filter. The zero-cross points of filter output correspond to the peak of filter input signal. The step instance is determined by finding the zero-cross point from positive to negative transition.

Figure 15:
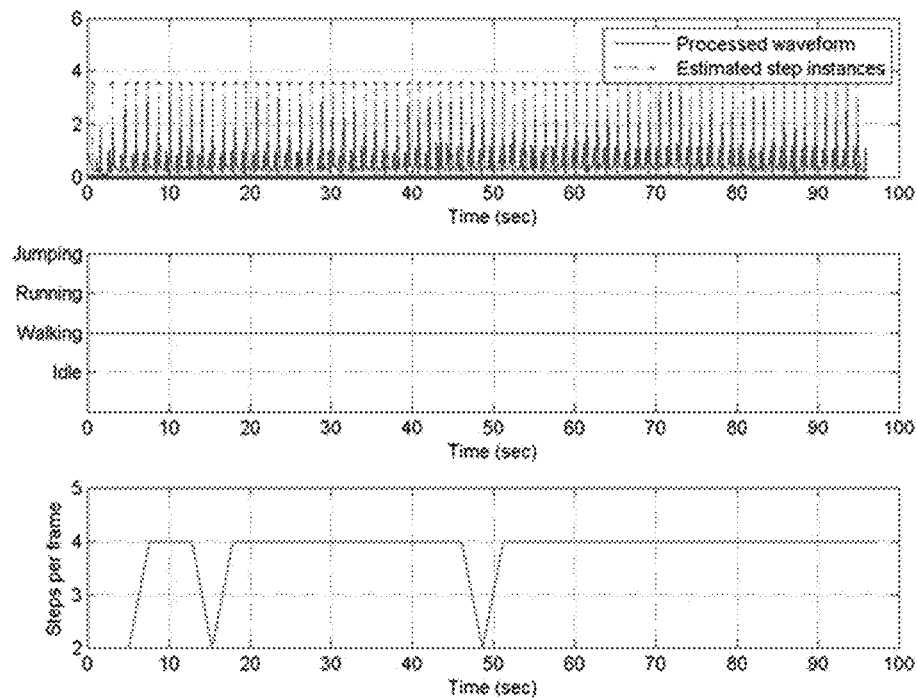
FIGS. 15 and 16 show an example of the performance of the activity classifier and the step counter for one sample data log for walking activity with sensor placed on shoe and on wrist respectively.
Figure 16:
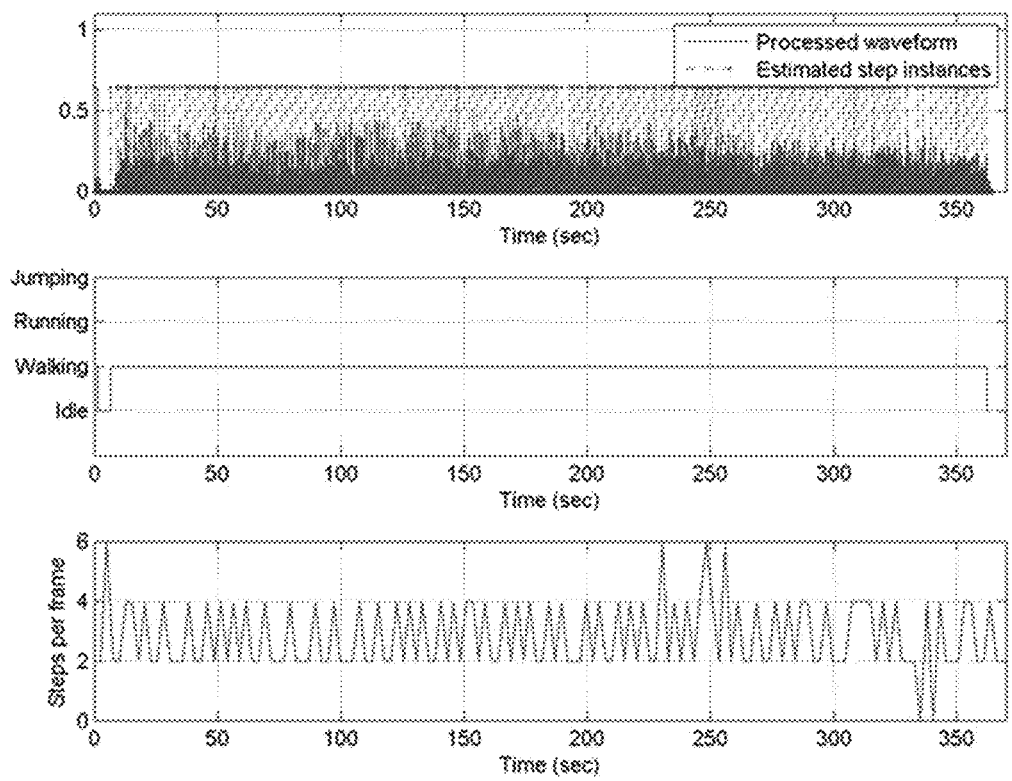

FIG. 15 and FIG. 16 show the performance of the classifier 170 and the step counter 160 for one sample data log for walking activity with sensor placed on shoe and on wrist respectively. Post-processing to refine the outputs was not used in this simulation. The top plot shows the input to the step counter module 160 overlaid with the step instances as determined by the step counter 160. As can be observed from the plots, there is a good correlation between the two indicating that the step counter 160 detects the step instances very reliably. There are occasional false detects, especially at activity transition, which can be addressed in the post-processor. The middle plot in these figures show the estimated activity and this also corresponds very well with the logged activity information. The bottom plot shows the number of steps in each frame. In all the results presented in this document, the frame size is 128 samples which results in a time period of 2.56 seconds for 50 Hz sampling rate.

The above description is presented to enable a person of ordinary skill in the art to practice the present invention as provided in the context of a particular application and its requirement. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention claimed is:

1. A system for counting steps, the system comprising:
a three-dimensional (3-D) accelerometer sensor-circuitry including sensor circuits configured and arranged to generate and output accelerometer data associated with three perpendicular axes;
pre-processor circuitry coupled to the 3-D accelerometer sensor-circuitry configured and arranged to produce filtered accelerometer data;
dominant component computation circuitry coupled to the pre-processor circuit, wherein the dominant component computation circuit is configured and arranged to identify a dominant component among vertical and horizontal component data in the output of the 3-D accelerometer sensor-circuitry; and
step counter circuitry configured and arranged to count a number of steps using the output of the dominant component computation circuit, wherein the step counter circuit includes a Fast Fourier Transform (FFT) circuit and a direct current (DC) remover circuit configured and arranged to remove a static component from an output of the FFT circuit, an activity frequency selector circuit, a derivative filter circuit and a zero crossing detector circuit.

2. The system of claim 1, further comprising a statistics generator module, including circuitry, coupled to the dominant component computation circuitry and the pre-processor circuitry.

3. The system of claim 2, further comprising a classifier, including circuitry, configured and arranged to determine an activity based on outputs of the dominant component computation circuitry and the statistics generator module.

4. The system of claim 3, wherein the step counter circuitry is configured to refine an output of the step counter circuitry based on an output of the classifier.

5. The system of claim 1, further including post-processor circuitry that is configured to refine an output of the step counter circuitry.

6. The system of claim 2, wherein the statistics generator module includes a first statistics circuit and a second statistics circuit, wherein the first statistics circuit-is configured to generate statistics and frequency domain transformation based on an output of the dominant component computation circuitry and the second statistics circuit is configured to generate statistics and frequency domain transformation based on an output of the pre-processor circuitry.

7. The system of claim 1, wherein the pre-processor circuitry is configured to remove at least one of a direct current (DC) component in a vector sample received from the 3-D accelerometer sensor-circuitry and a high frequency component from the vector sample.

8. The system of claim 7, wherein the dominant component computation circuitry is configured to determine a dominant component in the vector sample.

9. The system of claim 8, wherein the vector sample includes the horizontal component data and the vertical component data.

10. The system of claim 9, wherein the vertical component data is proportional to a vector inner product between a mean vector of a plurality of vector samples along three axes and each dynamic vector corresponding to a first difference between each of the plurality of vector samples and the mean vector.

11. The system of claim 10, wherein the horizontal component data is related to a norm of a second difference between the first difference and the mean vector scaled by the vertical component data.

12. The system of claim 1, wherein the pre-processor circuitry includes at least one of a level normalization circuit, a DC notch filter circuit and a low pass filter circuit.

13. The system of claim 1, further including an activity classifier circuit, wherein the activity classifier circuit is configured and arranged to refine an output of the step counter circuitry.

14. The system of claim 13, wherein the activity classifier circuit is embodied in an external device that is configured and arranged to communicate with the step counter circuitry.

15. A non-transitory computer readable medium having programming instructions stored thereon which, when executed by a processor, cause the processor to perform a method including:
receiving an output from three-dimensional (3-D) accelerometer sensor-circuitry, including sensor circuits, configured and arranged to generate and output accelerometer data associated with three perpendicular axes;
pre-processing the received output of the 3-D accelerometer sensor-circuitry, wherein the pre-processing includes removing a direct current (DC) component from the output of the 3-D accelerometer sensor-circuitry;
determining a dominant component among vertical component data and horizontal component data in the output of the 3-D accelerometer sensor-circuitry after the pre-processing, wherein the output of the 3-D accelerometer sensor-circuitry is used to derive the vertical component data and the horizontal component data, the vertical component data is proportional to a vector inner product between a mean vector of a plurality of vector samples along the three perpendicular axes and each dynamic vector corresponding to a first difference between each of the plurality of vector samples and the mean vector, wherein the horizontal component data is related to a norm of a second difference between the first difference and the mean vector scaled by the vertical component data; and
counting steps using the dominant component, wherein the counting includes performing a Fast Fourier Transform (FFT) and zero crossing detection.

16. The computer readable medium of claim 15, further including programming instructions, which when executed by the processor, cause the processor to collect statistical data based on at least one of a time domain data and frequency domain data derived from the accelerometer data or the dominant component, and determining an activity type.

17. The computer readable medium of claim 16, wherein the counting is refined to remove false steps using the activity type.

18. The computer readable media of claim 15, wherein the operation further includes removing a high frequency component from the vector sample.

19. The computer readable medium of claim 15, wherein determining the dominant component includes determining in a vector sample in the plurality of vector samples, wherein the vector sample includes the horizontal component data and the vertical component.

20. The computer readable medium of claim 19, wherein the vertical component data is proportional to a vector inner product between a mean vector of a plurality of vector samples along three axes and each dynamic vector corresponding to a first difference between each of the plurality of vector samples and the mean vector.

* * * * *